United States Patent [19]
Kishimoto et al.

[11] Patent Number: 5,866,689
[45] Date of Patent: Feb. 2, 1999

[54] MONOCLONAL ANTIBODIES TO GP130 PROTEIN

[75] Inventors: Tadamitsu Kishimoto, 5-31, Nakano-cho 3-chome, Tondabayashi; Daisuke Miki, Machida; Takashi Saito, Kanagawa; Kiyoshi Yasukawa, Sagamihara; Hiroshi Suzuki, Ebina, all of Japan

[73] Assignees: Tosoh Corporation, Shinnanyo; Tadamitsu Kishimoto, Osaka, both of Japan

[21] Appl. No.: 794,282

[22] Filed: Feb. 3, 1997

Related U.S. Application Data

[63] Continuation of Ser. No. 325,061, Oct. 19, 1994, abandoned, which is a continuation of Ser. No. 52,735, Apr. 27, 1993, abandoned.

[30] Foreign Application Priority Data

Apr. 28, 1992 [JP] Japan ..................................... 4-134329

[51] Int. Cl.⁶ .......................... C07K 16/00; C07K 16/28; C12N 5/18
[52] U.S. Cl. .................................. 530/388.2; 530/388.22; 530/388.23; 530/388.25; 435/332; 435/334; 435/337; 424/152.1
[58] Field of Search ......................... 530/388.22, 388.25, 530/388.23, 388.2; 435/70.21, 344.1, 332, 334, 337; 424/152.1

[56] References Cited

FOREIGN PATENT DOCUMENTS

A-0 411 946  2/1991  European Pat. Off. .
411 946      2/1991  Japan .

OTHER PUBLICATIONS

Hirano et al. "Biological and clinical aspects of interleukin 6," *Immunology Today* 11(12):443–449 (1990).
Hirata et al. "Characterization of IL–6 Receptor Expression By Monoclonal And Polyclonal Antibodies," *Journal of Immunology* 143(9):2900–2906 (Nov. 1, 1989).
Ip et al. "CNTF and LIF Act on Neuronal Cells via Shared Signaling Pathways That Involve the IL–6 Signal Transducing Receptor Component gp130," *Cell* 69:1121–1132 (Jun. 26, 1992).
Kishimoto et al. "Antibody Against gp130 Protein," *Patent Abstracts of Japan* 15(500):C–0895 (Dec. 18, 1991).
Klein et al. "Interleukin 6 is the central tumor growth factor in vitro and in vivo in multiple myeloma," *Eur. Cytokine Net.* 1(4):193–201 (Oct.–Nov. 1990).
Liu et al. "Interleukin–6 Signal Transducer gp 130 Mediates Oncostatin M Signalling," *The Journal of Biological Chemistry* 267(24):16763–16766 (Aug. 25, 1992).
Suzuki et al. "Anti–murine IL–6 receptor antibody inhibits IL–6 effects in vivo," *Immunology Letters* 30:17–22 (1991).
Suzuki et al. "Anti–human interleukin–6 receptor antibody inhibits human myeloma growth in vivo," *Eur. J. Immunol.* 22:1989–1993 (1992).
Thorpe, "Monoclonal antibodies: clinical and regulatory issues," *TIBTECH* 11:40–42 (Feb. 1993).
Yasukawa et al. "Association of recombinant soluble IL–6–signal transducer, gp130, with a complex of IL–6 and soluble IL–6 receptor, and establishment of an ELISA . . ." *Chem. Abstr.* 116:149749x (1992).
Search Report for corresponding European application EP–93–30–3276.
Harris et al. "Therapeutic antibodies—the coming of age," *TIBTECH* 11:42–44 (Feb. 1993).
Hibi et al. "Molecular Cloning and Expression of an IL–6 Signal Transducer, gp130," *Cell* 63: 1149–1157 (Dec. 21, 1990).
Osband et al. "Problems in the investigational study and clinical use of cancer immunotherapy," *Immunology Today* 11: 193–195 (1990).
Rein, "Another sepsis drug down—Immunex' TNF receptor," *Biotechnology Newswatch*, 1,3 (Oct. 4, 1993).
Taga et al. "Functional inhibition of hematopoietic and neurotrophic cytokines by blocking the interleukein 6 signal transducer gp130," *Proc. Nat'l Acad. Sci. USA* 89:10998–11001 (Nov. 1992).
Winter et al. "Man–made antibodies," *Nature* 349: 293–299 (Jan. 24, 1991).
Yasukawa et al. "Association of recombinant soluble IL–6–signal transducer, gp130, with a complex of IL 6 and soluble IL–6 receptor, and establishment of . . .," *Immunology Lett.* 31: 123–130 (Feb. 1992).

*Primary Examiner*—Frank C. Eisenschenk
*Attorney, Agent, or Firm*—Foley & Lardner

[57] ABSTRACT

Monoclonal antibodies recognizing gp130 protein and binding to the protein to inhibit IL-6 functions completely (that is to the same level as that is the absence of IL-6) when present in enough amount; a hybridoma producing the monoclonal antibody; a process for production of the monoclonal antibodies using the hybridoma; and an inhibitory agent for inhibition of physiological actions of IL-6 comprising the monoclonal antibodies.

17 Claims, 5 Drawing Sheets

MONOCLONAL ANTIBODIES TO GP130 PROTEIN

This application is a continuation, of application Ser. No. 08/325,061, filed Oct. 19, 1994, now abandoned, which is a continuation of Ser. No. 08/052,735, filed Apr. 27, 1993, now abandoned.

BACKGROUND OF THE INVENTION

1. Field of the Invention

The present invention relates to monoclonal antibodies to gp130 protein responsible for transmission of interleukin-6 (IL-6).

2. Related Art

IL-6 binds to interleukin-6 receptor (IL-6R) (Japanese Unexamined Patent Publication (Kokai) No. 2-288898) to form a complex. The complex of the IL-6 and IL-6R binds to gp130 protein which is a membrane protein on a target cell (Japanese Unexamined Patent Publication (Kokai) No. 4-29997) to transmit various physiological actions of IL-6 to a target cell (Taga et al., Cell 58, p573 (1989)).

As a physiological action of IL-6, a platelet increasing action was reported (Ishibashi et al., Blood 74, 1241, 1989), and therefore IL-6 is expected to be a novel pharmaceutical component. On the other hand, it was reported that abnormal production of IL-6 causes various autoimmune diseases, and inhibitors of this physiological action have attracted much attention. (Hirano et al., Immunology Today, 11, 443, 1990). As one such IL-6 inhibitors, it was reported that antibodies to IL-6 provide therapeutic effects on terminal myeloma patients (B. Klein et al., Eur. Cytokine Net. 1, 193, 1990).

As IL-6 inhibitors, in addition to antibodies to IL-6, antibodies to gp130 which is a protein transmitting an IL-6 signal, i.e., physiological activity of IL-6, are anticipated. Moreover, it is reported that the gp130 protein is a signal transmitting protein for oncostatin M which is a cancer cell growth factor and a signal transmitting protein for a leukemia inhibitory factor (LIF) which was originally identified as a leukemia growth inhibitor (Gearing et al., Science, 255, 1434, 1992), and therefore antibodies to gp130 protein are promising as an inhibitor for these physiologically active substances.

As antibodies to gp130 protein, Japanese Unexamined Patent Publication (Kokai) No. 3-219894 describes antibodies AM64 and AM277 prepared from mice immunized with gp130 protein. However, inhibitory effects of the known antibodies such as AM64 and AM277 on IL-6 functions are partial, indicating that the known antibodies could not be used as inhibitors of IL-6. Establishment of hybridomas producing anti-gp130 antibody which can inhibit IL-6 functions as strongly as the known antibody against IL-6 (MH166, see Matsuda et al., Eur. Immunol. 18, 951, (1988).) or IL-6R (PM1, see Hirata et al., 143, 2900, (1989)) seems to be difficult to be accomplished because (1) anti-gp130 monoconal antibody which inhibit IL-6 functions strongly cannot be necessarily prepared, (2) the efficient method of selecting the hybridoma producing desired antibody from a large number of established clones is not known. (It is impossible to check precisely the inhibitory effects on IL-6 functions by using the supernatant containing antibody.) (3) although genetic engineered soluble gp130 lacking transmembrane and cytplasmic regions can be used instead of membrane-purified gp130, it is not reported that such soluble gp130 is suitable as immunogen to prepare above said antibody.

DISCLOSURE OF THE INVENTION

Accordingly, the present inventors immunized mice with a recombinant gp130 protein, established a lot of hybridomas producing antibodies which recognize gp130 protein, and screened the hybridomas to obtain hybridomas producing antibodies which completely inhibit the physiological actions of IL-6.

Accordingly, the present invention provides monoclonal antibodies which specifically recognize gp130 protein and inhibit IL-6 functions completely (that is to the same level as that in the absence of IL-6), when present in enough amount, namely when the monoclonal antibody is present in an excess amount relating to gp130 protein, and more specifically inhibit signal transmission between IL-6 and gp130.

The present invention also provides hybridomas which produce the above-mentioned monoclonal antibodies.

The present invention further provides a process for production of the above-mentioned monoclonal antibodies comprising culturing the above-mentioned hybridomas.

The present invention still further provides an inhibitor for physiological action of IL-6, comprising the above-mentioned monoclonal antibody.

DETAILED DESCRIPTION

Figure 1:
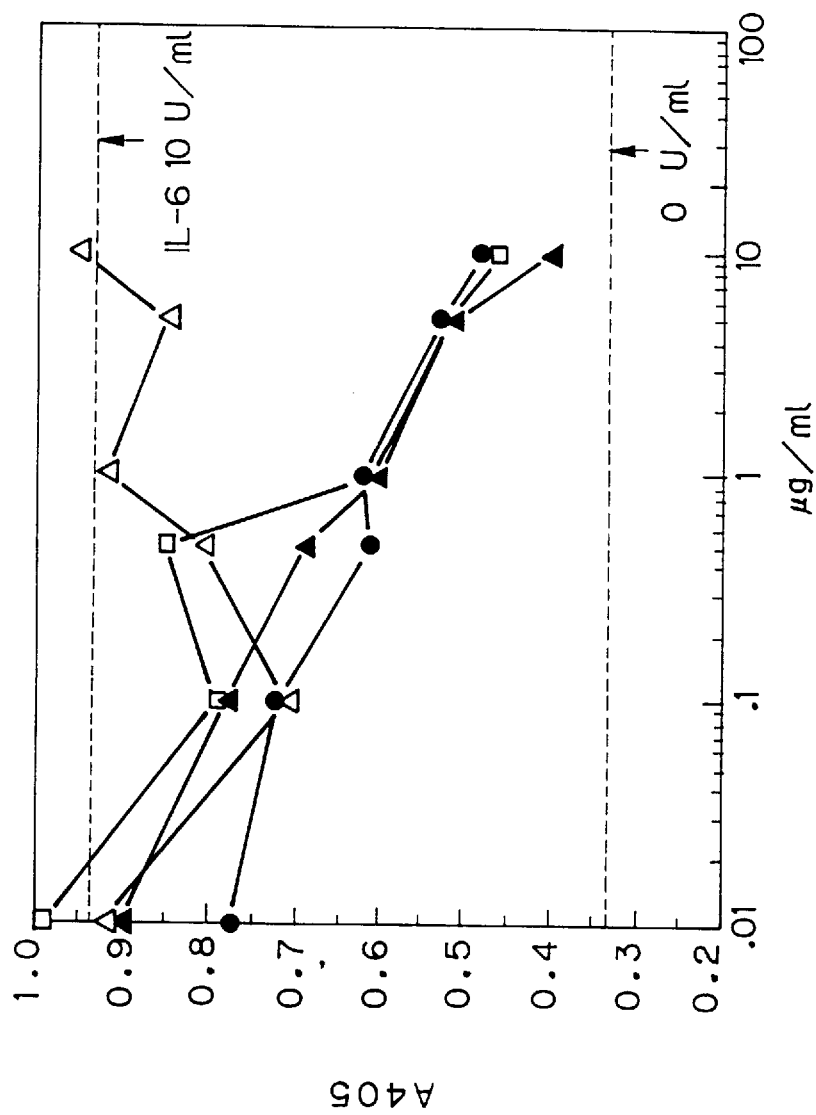
FIG. 1 represents the action of the present monoclonal antibodies to inhibit an antibody production inducing activity of human B cell line CL4, as described in Example 2, wherein the axis of the abscissa shows the amount of antibody added in μg/ml, and the axis of the ordinate shows an antibody productivity in the absorption at 405 nm. In this figure, the upper and lower dotted lines show results obtained by adding IL-6 in an amount of 10 U/ml or 0 U/ml, respectively, without adding an antibody. The symbols -●-, -▲-, -□-, and -Δ- represent results of GPX 22 antibody, GPZ 35 antibody, PM1 antibody and mouse immunoglobulin, respectively.

The present monoclonal antibodies are produced using an antigen, gp130 protein, which is a glycoprotein binding IL-6R in the presence of IL-6, but not binding IL-6R in the absence of IL-6, and showing an apparent molecular weight of 130 kDa as determined by SDS-acrylamide gel electrophoresis.

The present monoclonal antibodies are produced by hybridoma cell lines constructed by immunizing an animal such as mouse with an antigen, obtaining spleen cells from the immunized animal, hybridizing the spleen cells with established myeloma cells such as SP2/0 cell line, and cloning cell lines producing a desired monoclonal antibody. The antigen is, for example, a recombinant gp130 protein (soluble type) prepared according to, for example, a procedure described in Yasukawa et al., Immunol. Lett. 31, 123 (1992).

Preferred hybridoma of the present invention are, for example, hybridoma GPZ 35, deposited with Fermentation Research Institute, Agency of Industrial Science and Technology (FRI), 1-3 Higashi 1-chome, Tsukuba-shi, Ibaraki, 305 Japan, as FERM P-12940, on Apr. 27, 1992, and transferred to an international deposition under the Budapest Treaty as FERM BP-4263, on Apr. 15, 1993; GPX 7 deposited with FRI as FERM P-12938 on Apr. 27, 1992, and transferred to an international deposition under the Budapest Treaty as FERM BP-4261, on Apr. 15, 1993; and GPX 22 deposited with FRI as FERM P-12939 on Apr. 27, 1992, and transferred to an international deposition under the Budapest Treaty as FERM BP-4262, on Apr. 15, 1993.

Monoclonal antibodies produced by the above-mentioned hybridomas bind to gp130 protein so as to more completely inhibit physiological action of IL-6 in comparison with known monoclonal antibodies AM64, and AM277. Moreover, these monoclonal antibodies react with native gp130 protein isolated from cell membrane, serum or urine, as well as recombinant gp130 protein used as an antigen for immunizing a mouse.

The present monoclonal antibody is produced by culturing in-vitro the above-mentioned hybridoma in a conventional medium under conventional conditions. Alternatively, the present monoclonal antibody can be produced in-vivo by intraperitoneally inoculating the above-mentioned hybridoma into an animal such as a mouse, and recovering the ascites from the animal. Where more than one hybridoma is cultured, a mixture of more than one monoclonal antibody may be obtained.

The monoclonal antibody of the present invention in a culture medium or ascites can be purified by, for example, ammonium sulfate precipitation, affinity chromatography using a gel to which gp130 protein has been immobilized, and the like, alone or in combination.

As described above, the present antibodies bind to gp130 protein resulting in inhibition of physiological action of IL-6. Accordingly, the present monoclonal antibodies can be used to prepare an inhibitory agent for physiological action of IL-6. Moreover, the present monoclonal antibodies are promising as inhibitors to physiologically active substances for whose signal transmission gp130 protein is involved.

EXAMPLE

Next, the present invention is explained in detail by means of but not limited to Examples.

Example 1
Preparation of monoclonal antibodies GPZ 35, GPX 7 and GPX 22

A BALB/c mouse was intraperitoneally immunized with a recombinant gp130 protein prepared from CHO cells according to Yasukawa et al., Immunol. Lett. 31, 21 (1992) by administering 50 μg each of the recombinant gp130 protein 4 times every ten days. Spleen cells were obtained from the mouse and were hybridized with myeloma cells (SP2/0 line) using polyethylene glycol.

The cells subjected to the cell fusion were cultured in DMEM, HAT medium, and allowed to produce a monoclonal antibody in the medium to screen the cells for monoclonal antibody production. Namely, the recombinant gp130 protein (soluble type) used as an immunogen was immobilized to each well of a 96-well plate, and a supernatant of the culture and an alkaline phosphatase-conjugated anti-mouse immunoglobulin antibody were added thereon to determine the presence of monoclonal antibody recognizing gp130 protein. Next, for the cultures wherein the presence of monoclonal antibody recognizing gp130 protein was confirmed, cells were cloned by a limiting dilution method. In this way, eventually, 66 clones which produce a monoclonal antibody recognizing gp130 protein were established.

The 66 clones thus obtained were tested as follows. First, anti-human gp130 protein monoclonal antibody AM64 of mouse origin (Japanese Unexamined Patent Publication (Kokai) No. 3-219894) was immobilized in each well of a 96-well plate. Next, gp130 protein of CHO cell origin (soluble type, see above) was added thereon to immobilize the gp130 protein via the immobilized monoclonal antibody AM64. To each well, were simultaneously added a mixture of recombinant IL-6 prepared from E. coli (Yasukawa et al., Biotech. Lett. 12, 419, 1990) and recombinant IL-6R (Yasukawa et al. J. Biochem. 108, 673, 1990), and a culture supernatant of each hybridoma. Next, to determine an ability of the added monoclonal antibody to inhibit the formation of ternary complex of IL-6, IL-6R and gp130 of IL-6, anti-IL-6R polyclonal antibody prepared by immunizing a guinea pig with IL-6R and an alkaline phosphatase-labeled anti-guinea pig immunoglobulin antibody were added to each well to allow reaction of the added anti IL-6R polyclonal antibody with the IL-6R immobilized via AM64 monoclonal antibody and gp130 protein. Next, each well was washed, and a substrate for the alkaline phosphatase was added thereon.

As a result, among the above-mentioned 66 clones, three clones, i.e., GPZ 35, GPX 7, and GPX 22 produced a monoclonal antibody exhibiting inhibitory action on physiological action of IL-6.

Example 2
Effect of anti-gp130 protein monoclonal antibody to inhibit action of IL-6 to induce antibody production by human B cell line CL4

The hybridomas GPZ 35 and GPX 22 constructed in Example 2 were separately intraperioneally inoculated into BALB/c mice to prepare the ascites containing monoclonal antibodies GPZ 35 and GPX 22 respectively, and the monoclonal antibodies were purified. Anti-IL-6R antibody PM1, which inhibits IL-6-functions (Hirano et al., J. Immunol. 143, 2900 (1989), was used as a positive control.

CL4 cells (T. Hirano et al., Pro. Natl. Acad. Sci. U.S.A., 82, 5490, 1985) respond to IL-6 by producing immunoglobulin. A suspension of CL4 cells was distributed to each well of a 96-well plate so that each well contains $1 \times 10^4$ cells in 0.2 ml, and various dilutions of the monoclonal antibodies or mouse immunoglobulin as a control as well as 10 U/ml IL-6 were added to the well, and the cells were cultured in RPM 11640 medium for 3 days. After the culturing, the amount of immunoglobulin produced was measured by enzyme immunoassay (ELISA).

As a result, when the monoclonal antibody GPZ 35, GPX 22 or PM1 was added, antibody production by CL4 cells was inhibited in a dose-dependent manner, however, when mouse immunoglobulin was added as a control, the CL4 cell antibody production was not inhibited. This result demonstrates that the present monoclonal antibodies recognize gp130 protein and inhibit physiological action (action to induce antibody production of CL4 cells) of IL-6 as strongly as PM1. The result is shown in FIG. 1.

Example 3
Ability of anti-gp130 protein monoclonal antibody to inhibit a human T cell KT3 growth inducing action of IL-6

The hybridomas GPZ 35, GPX 7 and CPX 22 were separately intraperitoneally inoculated into BALB/c mice, ascites containing monoclonal antibody was obtained, and the monoclonal antibodies GPZ 35, GPX 7 and GPX 22 were purified.

The T cell KT3 line (Y. Hirata et al., J. Immunol. 143, 2900, 1989) grows by physiological action of IL-6. A suspension of a T cell KT3 line was distributed to each well of a 96-well plate so that each well contained $2 \times 10^4$ cells in 0.2 ml, and various dilutions of the monoclonal antibodies or mouse immunoglobulin as control, as well as 0.25 U/ml IL-6 were added, and the cells were cultured in a RPMI 1640 medium for 3 days. After the culturing, the number of cells in each well was measured by the MTT method using a commercially available kit (Chemicon).

As a result, where monoclonal antibody GPZ 35, GPX 7 or GPX 22 was added, the number of differentiated cells was decreased depending on the concentration of the added monoclonal antibody, while where mouse immunoglobulin as a control was added, the number of cells was not decreased. This result demonstrates that the present monoclonal antibodies recognize gp130 protein, and inhibit physiological action (action to induce the growth of the T cell KT 3 line) of IL-6.

Figure 2:
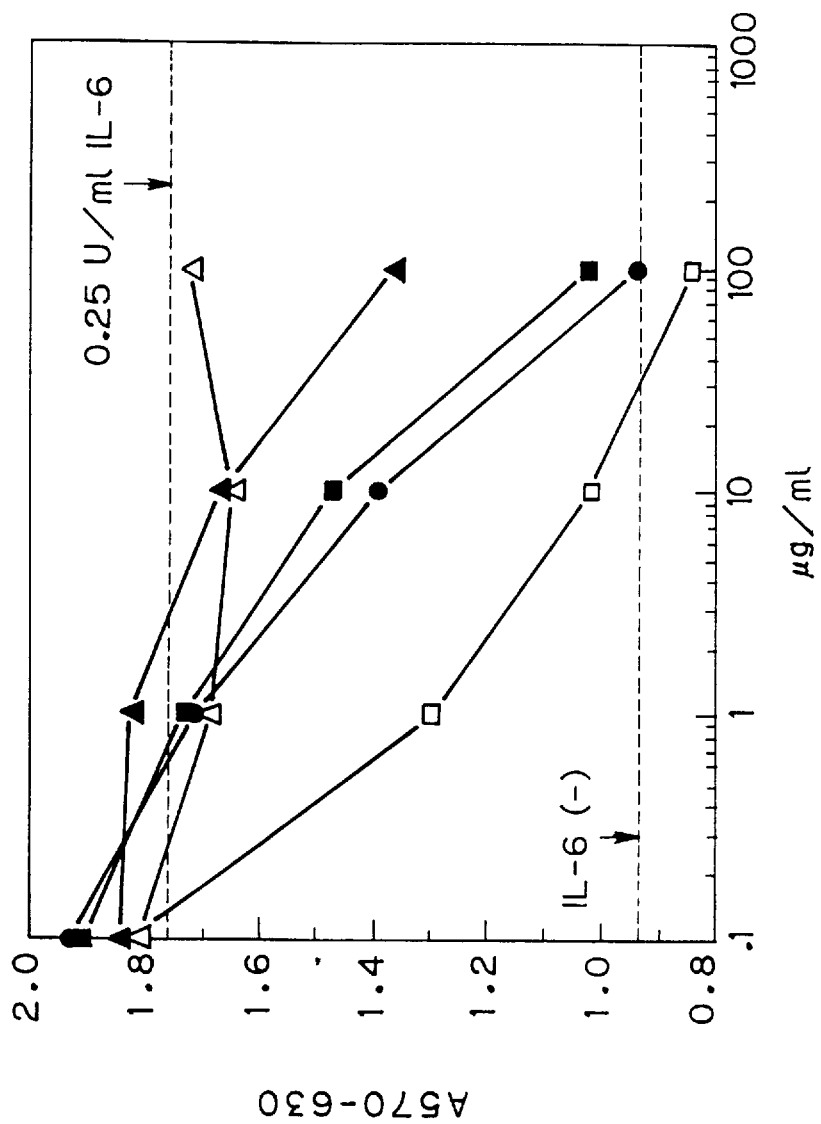
FIG. 2 represents the action of the present antibodies to inhibit growth-inducing action of human T cell KT3, as described in Example 3, wherein the axis of the abscissa shows the amount of antibody added in μg/ml, and the axis of the ordinate shows the number of cells represented by the absorption at 570 to 630 nm. In this figure, the upper and lower dotted lines show results obtained by adding IL-6 in an amount of 0.25 U/ml or 0 U/ml, respectively, without adding the antibody. The symbols -●-, -■-, -▲-, -□-, and -Δ- represent results of GPX 22 antibody, GPX 7 antibody, GPZ 35 antibody, PM1 antibody and mouse immunoglobulin, respectively.
Figure 3:
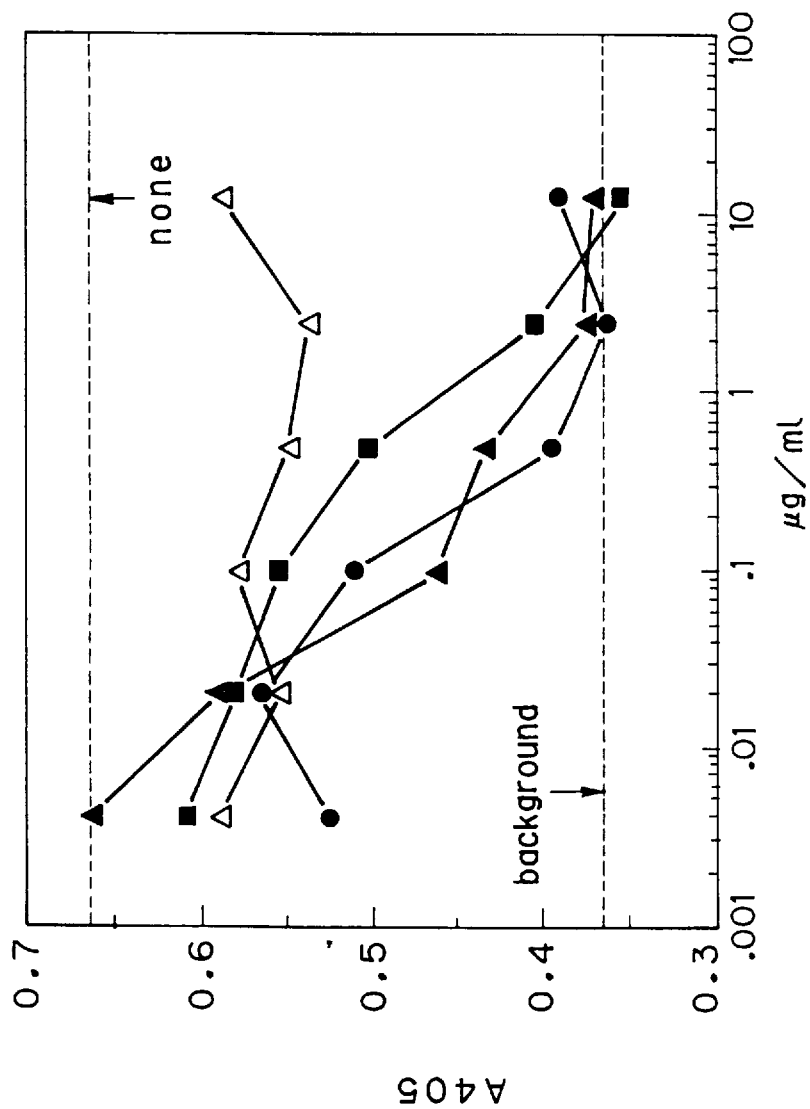
FIG. 3 represents the action of the present antibodies to inhibit binding of a complex of IL-6 and IL-6R to gp130 protein, as described in Example 4, wherein the axis of the abscissa shows an amount of antibody added in μg/ml, and the axis of the ordinate shows an amount of IL-6R bound to gp130 protein in the absorbance at 405 nm. In this figure the upper and lower dotted lines show a result obtained without adding the antibody and the background respectively. The symbols -●-, -■-, -▲-, and -Δ- show results of GPX 22 antibody, GPX 7 antibody, GPZ 35 antibody and mouse immunoglobulin respectively.

The result is shown in FIG. 2.

Example 4
Effect of anti-gp135 protein monoclonal antibody to inhibit binding of IL-6 and IL-6R to gp130 protein Hybridoma GPZ 35, GPX 7 and GPX 22 were separately intraperitoneally inoculated into BALB/c mice, the ascites containing monoclonal antibody was obtained, and the monoclonal antibodies GPZ 35, GPX 7 and GPX 22 were purified.

Anti-human gp130 protein monoclonal antibody AM64 of mouse origin was immobilized to each well of a 96-well plate, and recombinant gp130 protein prepared using CHO cells was added thereon allowing it to bind to the immobilized monoclonal antibody AM64. Next, to a mixture of recombinant gp130 protein prepared using CHO cells and recombinant IL-6R (soluble type) prepared using CHO cells, various dilutions of the monoclonal antibody or mouse immunoglobulin control were simultaneously added. Note, the amounts of IL-6 and IL-6R were 5 µg/ml.

Next, to determine the effect of the added anti-gp130 protein monoclonal antibody, both anti-IL-6R polyclonal antibody, prepared by immunizing a guinea pig with IL-6R, and alkaline phosphatase-labeled anti-guinea pig immunoglobulin antibody were added to each well to allow the added anti-IL-6R polyclonal antibody to react with any IL-6R immobilized via AM64 monoclonal antibody and gp130 protein. Next, each well was washed, and a substrate for alkaline phosphatase was added.

As a result, where the monoclonal GPZ 35, GPX 7 or GPX 22 was added, the signal, i.e., IL-6R which was bound to gp130 protein, was decreased depending on the amount of the added monoclonal antibody, while where mouse immunoglobulin was added, the signal was not decreased. This result demonstrates that the present monoclonal antibodies recognize gp130 protein and inhibit binding of IL-6 and IL-6R with gp130 protein.

Example 5
Effect of anti-gp130 protein monoclonal antibody to inhibit human myeloma growth accelerating action of IL-6

Hybridoma GPZ 35, GPX 7 and GPX 22 obtained in Example 1 were separately intraperitoneally inoculated into BALB/c mice, the ascites containing the monoclonal antibody was obtained, and the monoclonal antibodies GPZ 35, GPX 7 and GPX 22 were purified.

A suspension of human myeloma S6B45 cells (Okuno et al., Exp, Hematol. 20, 395, 1992), in which IL-6 was acting as an autocrine growth factor, was distributed to each well of a 24-well plate so that each well contained $5 \times 10^4$ wells in 0.5 ml, and various dilutions of the monoclonal antibody or mouse immunoglobulin as a control were added therein. The cells were cultured in a RPMI 1640 medium, and on the third day, the number of myeloma cells was measured by the MTT method using a commercially available kit (Chemicon).

Figure 4:
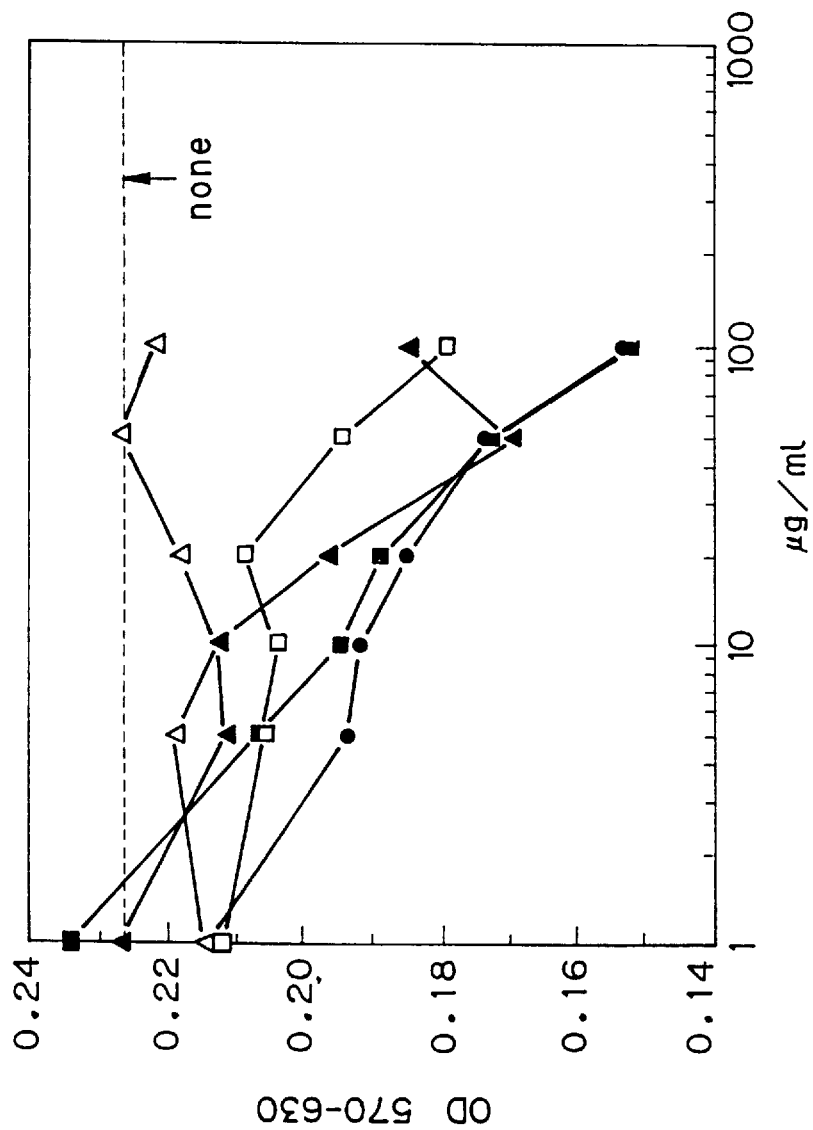
FIG. 4 represents the action of the present antibody to inhibit human myeloma growth accelerating action of IL-6, as described in Example 5, wherein the axis of the abscissa shows an amount of antibody added in μg/ml, and the axis of ordinate shows the number of cells represented by absorption at 570 to 630 nm. In this figure the dotted line shows a result obtained without adding the antibody. The symbols -●-, -■-, -▲-, -□-, and -Δ- show results of GPX 22 antibody, GPX 7 antibody, GPZ 35 antibody, PM1 antibody, and mouse immunoglobulin, respectively.

As a result, where the monoclonal antibody GPZ 35, GPX 7, GPX 22, or PM1 was added, the autocrine growth of the myeloma cells was inhibited depending on the concentration of the added monoclonal antibody, while where mouse immunoglobulin was added, the growth of myeloma cells was not inhibited. This result demonstrates that the present monoclonal antibodies recognize gp130 protein, and inhibit physiological action (autocrine growth of myeloma cells) of IL-6. The result is shown in FIG. 4.

Example 6
Effect of anti-gp130 protein monoclonal antibody to inhibit induction of growth of mouse BAF 130 cells in the presence of IL-6 and IL-6R The hybridoma GPZ 35, GPX 7 and GPX 22 obtained in Example 1 were separately intraperitoneally inoculated into BALB/c mice, the ascites containing the monoclonal antibody was obtained, and the monoclonal antibodies GPZ 35, GPX 7 and GPX 22 were purified.

Mouse BAF 130 cells were derived from mouse BAF cells (Hatakeyama et al., Cell, 63, 154,1989) which inherently do not express human gp130 protein, by transforming the mouse BAF cells with a gene coding for human gp130 protein. A suspension of the cells was distributed to each well of a 96-well plate so that each well contained $8 \times 10^4$ cells in 0.2 ml, and 250 ng/ml each of IL-6 and IL-6R were added thereon. In this condition, various concentrations of the monoclonal antibody or mouse immunoglobulin as a control was added, and the cells were cultured in RPMI 1640 for 2 days.

After the culturing, 750 nCi of $^3$H-thymidine was added to each well and after 6 hours, an amount of $^3$H-thymidine uptaken was measured by a scintillation counter.

Figure 5:
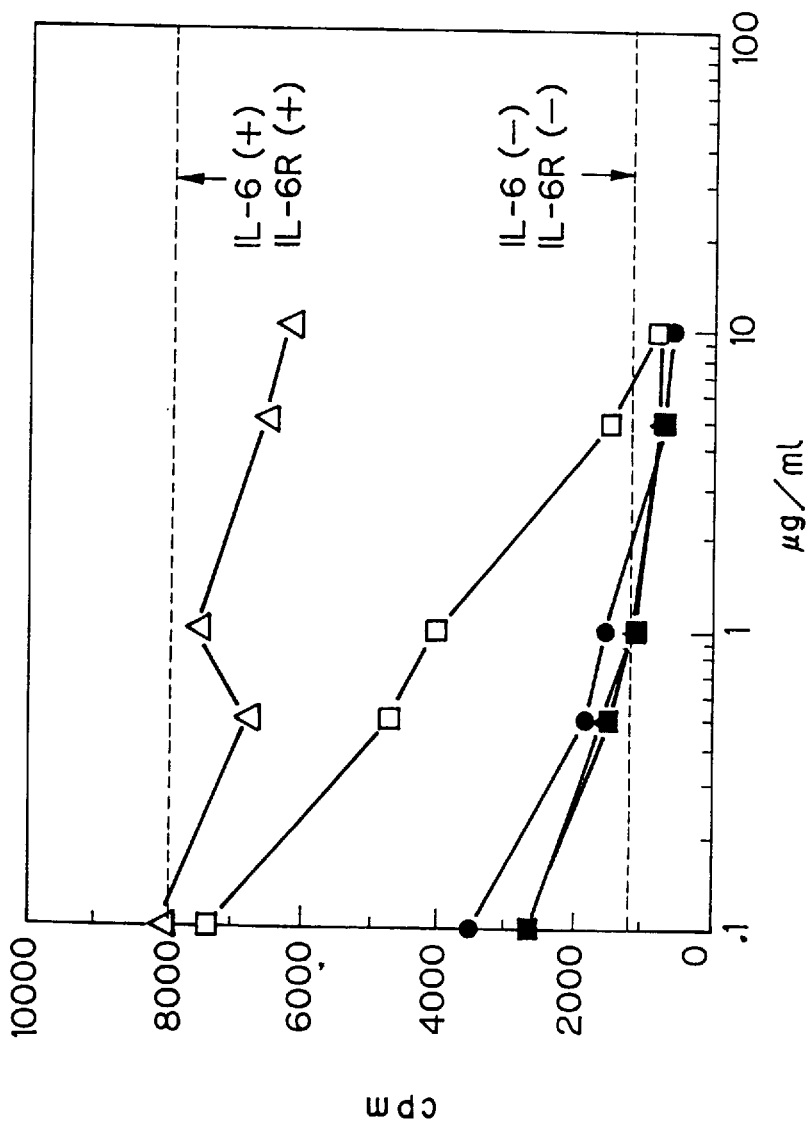
FIG. 5 shows the action of the present monoclonal antibody to inhibit growth inducing action on mouse BAF 130 cells in the presence of IL-6 and IL-6R, as described in Example 6, wherein the axis of the abscissa shows an amount of the antibody added, and the axis of the ordinate shows the growth of cells represented by uptake of $^3$H thymidine (cpm). In this figure, the upper and lower dotted lines show a result obtained by adding IL-6 and IL-6R without adding the antibody, and a result obtained without adding IL-6, IL-6R and the antibody, respectively. The symbols -●-, -■-, -▲-, -□-, and -Δ- represent results of GPX 22 antibody, GPX 7 antibody, GPZ 35, PM1 antibody antibody and mouse immunoglobulin, respectively.

As a result, where the monoclonal antibody GPZ 35, GPX 7, GPX 22 or PMI was added, a decrease of $^3$H-thymidine uptake was observed. That is, the monoclonal antibody inhibited the growth of mouse BAF 130 cells in a dose-dependent manner, whereas mouse immunoglobulin did not inhibit cell growth. This result demonstrates that the present monoclonal antibodies recognize gp130 protein, and inhibit physiological action (action to stimulate the growth of mouse BAF 130 cells) of IL-6. The result is shown in FIG. 5.

The present monoclonal antibodies such as GPZ 35, GPX 7 and GPX 22 recognize human gp130 protein and bind to said protein resulting in strong inhibition of physiological action of IL-6, and therefore are promising as an IL-6 inhibitory agent which inhibits physiological action of IL-6. This is impossible with known AM64 and AM266 monoclonal antibodies both recognizing gp130 protein. Therefore, the present invention, at first, provides monoclonal antibodies which can be used as a therapeutic agent for various diseases such as autoimmune diseases, myeloma and the like, which are caused by IL-6 or in which IL-6 is involved. Moreover, for example, the present monoclonal antibodies are promised as an inhibitor of physiologically active substances such as oncostatin M, a cancer cell-growth factor, and LIF, a leukemia growth inhibitory factor, which are considered to be involved in the signal transmission of IL-6.

The present monoclonal antibodies inhibit physiological action of IL-6 by binding to gp130 protein. Therefore, the present monoclonal antibody can be locally administered to positions at which the target cells are present to inhibit physiological actions of IL-6, while antibodies which inhibit physiological actions of IL-6 by binding IL-6 must be administered to positions at which IL-6 is present or must be targeted to positions at which IL-6 is present.

According to the present invention, the present monoclonal antibodies such as GPZ 35, GPX 7 and GPX 22 can be easily produced by culturing in-vitro a hybridoma such as GPZ 35, GPX 7 or GPX 22 in a medium or introperitoneally inoculating the hybridoma into an animal such as a mouse, and optionally recovering the produced monoclonal antibody.

We claim:

1. A monoclonal antibody that specifically binds gp130 protein of human origin, which is an interleukin-6 (IL-6) signal transmitting protein, and that is capable of inhibiting IL-6 functions to the same level as that in the absence of IL-6, when the monoclonal antibody is present in an excess amount relative to gp130 protein, wherein said antibody is selected from the group consisting of GPZ 35 antibody obtainable from hybridoma GPZ 35 (FERM BP-4263), GPX 7 antibody obtainable from GPX 7 (FERM BP-4261) and GPZ 22 antibody obtainable from GPZ 22 (FERM BP-4262).

2. A monoclonal antibody according to claim 1, wherein the monoclonal antibody is GPZ 35 antibody obtainable from hybridoma GPZ 35 (FEMB BP-4263).

3. A monoclonal antibody according to claim 1, wherein the monoclonal antibody is GPX 7 antibody obtainable from hybridoma GPX 7 (FERM BP-4261).

4. A monoclonal antibody according to claim 1, wherein the monoclonal antibody is GPX 22 antibody obtainable from hybridoma GPX 22 (FERM BP-4262).

5. Hybridoma producing a monoclonal antibody that specifically binds gp130 protein of human origin, which is an IL-6 signal transmitting protein, and that is capable of inhibiting IL-6 functions to the same level as that in the absence of IL-6, when the monoclonal antibody is present in an excess amount relative to gp130 protein, wherein said hybridoma is selected from the group consisting of GPZ 35 (FERM BP-4263), GPX 7 (FERM BP-4261) and GPZ 22 (FERM BP-4262).

6. Hybridoma according to claim 5, wherein the hybridoma is GPZ 35 (FERM BP-4263).

7. Hybridoma according to claim 5, wherein the hybridoma is GPX 7 (FERM BP-4261).

8. Hybridoma according to claim 5, wherein the hybridoma is GPX 22 (FERM BP-4262).

9. A process for the production of a monoclonal antibody that specifically binds gp130 protein of human origin, which is an IL-6 signal transmitting protein, and that is capable of inhibiting IL-6 functions to the same level as that in the absence of IL-6, when the monoclonal antibody is present in an excess amount relative to gp130 protein, comprising culturing a hybridoma producing said monoclonal antibody in-vitro or in-vivo, wherein said hybridoma is selected from the group consisting of GPZ 35 (FERM BP-4263), GPX 7 (FERM BP-4261) and GPZ 22 (FERM BP-4262).

10. A process according to claim 9, wherein the hybridoma is GPZ 35 (FERM BP-4263).

11. A process according to claim 9, wherein the hybridoma is GPX 7 (FERM BP-4261).

12. A process according to claim 9, wherein the hybridoma is GPX 20 (FERM BP-4262).

13. A composition for inhibiting a physiological action of IL-6 comprising, in combination with a carrier, a monoclonal antibody that specifically binds gp130 protein of human origin, which is an IL-6 signal transmitting protein, and that is capable of inhibiting IL-6 functions to the same level as that in the absence of IL-6, when the monoclonal antibody is present in an excess amount relative to gp130 protein, wherein said antibody is selected from the group consisting of GPZ 35 antibody obtainable from hybridoma GPZ 35 (FERM BP-4263), GPX 7 antibody obtainable from GPX 7 (FERM BP-4261) and GPZ 22 antibody obtainable from GPZ 22 (FERM BP-4262).

14. A composition according to claim 13, wherein the monoclonal antibody is that obtainable from hybridoma GPZ 35 (FERM BP-4263).

15. A composition according to claim 13, wherein the monoclonal antibody is that obtainable from hybridoma ZPX 7 (FERM BP-4261).

16. A composition according to claim 13, wherein the monoclonal antibody is that obtainable from hybridoma ZPZ 22 (FERM BP-4262).

17. The monoclonal antibody of claim 1, wherein said antibody is capable of inhibiting the IL-6 dependent growth of cells to the same level as that in the absence of IL-6, when the monoclonal antibody is present in an excess amount relative to gp130 protein, wherein said cells express human gp130 protein.

* * * * *